(12) United States Patent
Al-Zeer et al.

(10) Patent No.: US 9,981,056 B2
(45) Date of Patent: May 29, 2018

(54) AIR TREATMENT SYSTEM

(71) Applicant: MAZRA Incorporated, Houston, TX (US)

(72) Inventors: Mohammed Al-Zeer, Riyadh (SA); Abdulaziz Hamad Alzeer, Riyadh (SA); Troy Smith, Houston, TX (US)

(73) Assignee: MAZRA Incorporated, Houston, TX (US)

( * ) Notice: Subject to any disclaimer, the term of this patent is extended or adjusted under 35 U.S.C. 154(b) by 0 days. days.

(21) Appl. No.: 15/102,872

(22) PCT Filed: Nov. 25, 2015

(86) PCT No.: PCT/US2015/062628
§ 371 (c)(1),
(2) Date: Jun. 9, 2016

(87) PCT Pub. No.: WO2016/137550
PCT Pub. Date: Sep. 1, 2016

(65) Prior Publication Data
US 2017/0266335 A1    Sep. 21, 2017

Related U.S. Application Data

(60) Provisional application No. 62/126,103, filed on Feb. 27, 2015.

(51) Int. Cl.
*B01D 39/00* (2006.01)
*A61N 5/00* (2006.01)
(Continued)

(52) U.S. Cl.
CPC .................. *A61L 9/205* (2013.01); *A61L 9/18* (2013.01); *A61L 2209/111* (2013.01); *A61L 2209/14* (2013.01)

(58) Field of Classification Search
CPC ..... A61L 9/00; A61L 9/03; A61L 9/18; A61L 9/20; A61L 9/205
(Continued)

(56) References Cited

U.S. PATENT DOCUMENTS

| 3,984,296 A | 10/1976 | Richards |
| 4,071,334 A | 1/1978 | Kolb et al. |
| 4,695,358 A | 9/1987 | Clements et al. |
| 4,790,862 A * | 12/1988 | Naruo ...................... F24F 3/16 55/467 |

(Continued)

FOREIGN PATENT DOCUMENTS

| EP | 0931581 A1 | 7/1999 |
| JP | 2002-058728 A | 2/2002 |

(Continued)

*Primary Examiner* — Monzer R Chorbaji
(74) *Attorney, Agent, or Firm* — Invention To Patent Services; Alex Hobson (57) ABSTRACT

An air treatment system includes a particulate filtration portion and a disinfecting portion that may be configured within a single enclosure, such as a conduit. The disinfecting portion may include a UV light source that emits UV light onto the interior surface of the conduit that has a photocatalyst surface. A disinfecting portion may include an X-ray portion, wherein an X-ray emitter is configured within the conduit. In one embodiment, the X-ray emitter is configured to emit X-rays along the conduit and toward a photocatalytic mesh that is also configured within the conduit. The particulate filtration portion may be configured upstream of the disinfection portion.

22 Claims, 9 Drawing Sheets

(51) Int. Cl.
  *G01N 23/00* (2006.01)
  *A61L 9/20* (2006.01)
  *A61L 9/18* (2006.01)

(58) Field of Classification Search
  USPC ........ 422/32, 24; 250/455.11, 492.1, 370.09; 96/224
  See application file for complete search history.

(56) References Cited

U.S. PATENT DOCUMENTS

| | | |
|---|---|---|
| 5,973,904 A | 10/1999 | Chen et al. |
| 6,149,717 A | 11/2000 | Rinaldi et al. |
| 6,187,271 B1 | 2/2001 | Heo et al. |
| 6,468,428 B1 * | 10/2002 | Nishii .................... B01D 53/88 210/497.3 |
| 6,861,036 B2 | 3/2005 | Biswas et al. |
| 6,915,205 B2 | 7/2005 | Kim et al. |
| 7,767,169 B2 | 7/2005 | Parker et al. |
| 7,522,703 B2 | 4/2009 | Hino et al. |
| 7,796,727 B1 | 9/2010 | Kaufman |
| 2005/0269254 A1 | 12/2005 | Roitman |
| 2009/0151567 A1 * | 6/2009 | Krigmont ............... B03C 3/025 96/16 |
| 2009/0285362 A1 * | 11/2009 | Birnbach ................ A23L 3/263 378/122 |

FOREIGN PATENT DOCUMENTS

| | | |
|---|---|---|
| WO | 1990-09227 A1 | 8/1990 |
| WO | 2000-64818 A1 | 11/2000 |
| WO | 20007-102701 A1 | 9/2007 |

* cited by examiner

AIR TREATMENT SYSTEM

CROSS REFERENCE TO RELATED APPLICATIONS

This application claims the benefit and priority to U.S. provisional patent application No. 62/126,103 filed on Feb. 27, 2015; the entirety of which is incorporated by reference herein. This application also claims the benefit of the 371 application of PCT/US2015/062628 dated Nov. 25, 2015.

BACKGROUND OF THE INVENTION

Field of the Invention

The present invention relates to air treatment systems that filter, clean and disinfect air.

Background

Air quality has become more important with the better understanding of how both particulate contamination and biological aerosols can affect health. Many people gather in closed or semi-closed environments, such as transportation terminals and festival tents, where there is little air exchange and biological aerosols can become concentrated. There are devices that filter particulates from the air, and other devices that disinfect the air; however, there is a need for an efficient filtration system that both removes particulates and disinfects the air, using technology that allows size scaling for various types of occupied space.

Particulate contamination has been linked with many health issues including asthma, allergies and cancer. Exhaust from automobiles, industrial produced particulates and naturally occurring particulates in the air are known to be harmful to health.

Biological materials in the air, including viruses and bacteria, are an ever-increasing concern. Viruses can become airborne by coughing and sneezing, and many people are highly allergic to naturally occurring mold spores that can cause severe respiratory and other reactions. These biological contaminants move through the air, and in some cases through air handling systems, endangering the health of people gathered in tight quarters or confined spaces, such as airplanes, restaurants, and tents.

SUMMARY OF THE INVENTION

The invention is directed to an air treatment system that filters and disinfects the air. In an exemplary embodiment, the air treatment system is streamlined having both the particulate filtration and disinfecting portions in line, or in some cases configured in a modular format. In an exemplary embodiment, the particulate filtration portion is configured upstream of the disinfecting portion of the air treatment system. The air treatment system may comprise a particulate filtration portion at the leading end of the treatment system, or in a most upstream position, whereby particulates within the incoming airflow are removed before the air passes into a disinfecting portion of the air treatment system. In an exemplary embodiment, the air treatment system comprises a disinfecting portion comprising any suitable combination of disinfecting components including, but not limited to a UV treatment portion, a titanium dioxide ($TiO_2$) treatment portion and a soft X-ray portion.

A particulate filtration portion may comprise any suitable type of air filtration device or media. In an exemplary embodiment, a particulate filtration portion comprises an air filter having filtration media that is configured to filter out an incoming air stream to the air treatment system. Air filtration media may comprise any suitable type of filtration media including, but not limited to, felts, wovens, non-woven materials including spunbonded media, screens, electrostatic or tribo-electric media, charged media, microporous media, including fluoropolymers, expanded polytetrafluoroethylene (ePTFE), and the like. An air filtration media may comprise one, two, three or more layers of media that may be attached or otherwise arranged to provide high filtration efficiency. Any suitable combination of filtration media layers may be used. In an exemplary embodiment, the particulate filtration portion comprises a pleated filter, wherein the filtration surface area is increased by incorporating one, and more preferably, a plurality of pleats in the filtration media. In an exemplary embodiment, a pleated air filter is configured as an filtration cartridge, wherein airflow passes from a first inflow direction, perpendicular through the pleats of the filtration cartridge and then out of the cartridge. A pleated filter media has a higher surface area than a flat filter media configured in the same space or cross-sectional area, and provides less resistance to air flow.

An air filtration media may be configured to produce any suitable pressure drop of air through the particulate filtration portion. The airflow permeability of materials (Frazier) may be measured using a Fraziometer. A frazier value is the airflow rate in $(cm^3/cm^2)/s$ or $(cfm/ft2)/s$ passing through a sample at 12.7 mm, (0.5 inches) of water column pressure drop. The test is described in ASTM D737, and can be measured using part no. FAP0000LP from Qualitest Inc, Ft. Lauderdale, Fla. An air filtration material may have a frazier value (F) of greater than about 2 F, greater than about 10 F, greater than about 20 F, greater than about 40 F, greater than about 100 F and any range between and including the values provided. An air filtration with a higher frazier value will produce less pressure drop as the air flow therethrough and therefore will require less power to force the air through the system. A higher air permeability air filtration material is therefore preferred. In addition, the air filtration efficiency of the particulate filtration portion may be any suitable level including High-Efficiency Particulate Air (HEPA) and Ultra-Low Particulate Air (ULPA) filtration levels. HEPA efficiency is characterized in a 99.97% removal of 0.3 um or larger particles from an incoming airflow stream. ULPA efficiency is characterized in a 99.999% removal of 0.1 um particles or larger from an incoming airflow stream.

In an exemplary embodiment, the disinfecting portion of the air treatment system comprises a UV treatment portion. An exemplary UV treatment portion comprises at least one UV light source that is located and radiates UV light onto a periphery area, such as the inside surface of a flow conduit. A UV light source may be an elongated UV light source having a length at least three times greater than its cross-length dimension or more preferably at least 5 times greater than its cross-length dimension, or even more preferably at least 10 times greater than its cross-length dimension, or diameter. In an exemplary embodiment, a single elongated UV light source is centrally located within the flow conduit, with the length of the UV light source extending along the length of the flow conduit, and emits UV light around the outer perimeter of the light and onto the inside surface of the flow conduit. A single elongated light source that is centrally located may provide an effective distribution of the radiated UV light and sufficient exposure time. In another embodiment two elongated UV light sources extend along the length and within the flow conduit. The two light sources may be offset from each other within the interior of the flow conduit. An airflow may pass between the UV light source and the inside surface of the conduit where it will be exposed to the UV light as passes through the UV treatment portion. A UV light source may produce an suitable type of UV light, including those having the wavelength ranges described in Table 1:

| Name | Abbreviation | Wavelength range (nm) | Energy per photon |
|---|---|---|---|
| Ultraviolet A | UVA | 400-315 nm | 3.10-3.94 eV |
| Ultraviolet B | UVB | 315-280 nm | 3.94-4.43 eV |
| Ultraviolet C | UVC | 280-100 nm | 4.43-12.4 eV |
| Near Ultraviolet | NUV | 400-300 nm | 3.10-4.13 eV |
| Middle Ultraviolet | MUV | 300-200 nm | 4.13-6.20 eV |
| Far Ultraviolet | FUV | 200-122 nm | 6.20-10.16 eV |
| Hydrogen Lyman-Alpha | H Lyman-α | 122-121 nm | 10.16-10.25 eV |

A UV light source may draw any suitable amount of power and produce any suitable watts of total UV output. A UV output or power drawn from a UV light source may be more than about 4 watts, more than about 6 watts, more than about 10 watts, more than about 50 watts, more than about 100 watts, more than about 500 watts and any range between and including the values provided. In an exemplary embodiment, an elongated UV light source is configured within the air treatment system conduit with a length that extends along the length of the conduit. The length of the UV treatment portion, and/or the UV light source may be about 75% or more of the length of the disinfection portion, about 50% or more of the length of the disinfection portion and any range between and including the percentages provided. The length of the UV treatment portion, and/or the UV light source may be about 35% or more of the length of the conduit, about 50% or more of the length of the conduit and any range between and including the percentages provided.

In an exemplary embodiment, the disinfecting portion of the air treatment system comprises a photocatalyst, PCO, material. Photocatalytic oxidation is achieved by exposing a photocatalytic material to UV light. Any suitable type of photocatalyst may be configured within the conduit and exposed to the UV light source including, but not limited to, homogeneous photocatalysts, heterogeneous photocatalysts, metal oxides, nickel oxide, sodium tantalite, lanthanum, titanium dioxide, and any combination thereof. A surface, including the interior surface of the flow conduit, may be coated with a photocatalytic material, such as by painting the surface, and UV light may be incident on the surface. Incident UV rays on a $TiO_2$ surface create hydroxyl radicals and super-oxide ions, or highly reactive electrons. Bacteria, viruses, other organics materials and volatile organic compounds (VOC) react readily with the highly reactive electrons and are destroyed or converted into less harmful carbon dioxide and water molecules. This process causes degeneration of pollutants, bacteria and viruses, thereby purifying and cleaning the air. An air treatment system may act as an air cleaner wherein VOC's passing therethrough are destroyed. In an exemplary embodiment, a plurality of panels are configured about a UV light source, such that air passing through this disinfecting portion will be incident on the $TiO_2$ coated surfaces of the panels, thereby destroying any organic compounds in the airflow. In another embodiment, a UV light source produces UV light that is incident on a flow-through filter, such as a metal mesh that comprises PCO material, to destroy organic compounds as they pass through the fitter and come in contact with the PCO. A panel array may provide for a lower pressure drop through the system and the panels having a PCO material thereon may be configured as spokes about a centrally located UV light source.

In an exemplary embodiment, a photocatalytic surface comprises nanoparticles of titanium dioxide. These nanoparticles of titanium dioxide may be mixed with water and/or other binder material and coated, such as by painting or spraying, onto a surface to create a photocatalytic surface. A portion of the interior wall of the conduit may be coated with a photocatalyst and a UV light source may be configured within the conduit to project UV light onto the coated interior surface.

In an exemplary embodiment, the disinfecting portion of the air treatment system comprises an X-ray treatment portion. An X-ray emitter may be configured within an air treatment conduit and project X-rays substantially along the length, or along the air flow direction, of the conduit. An X-ray emitter configured within the conduit and within the airflow passing through the conduit may have improved performance as the airflow around the X-ray emitter will act to cool the emitter. This cooling effect from the conduit airflow may improve the reliability of the X-ray emitter and/or prolong the life of the X-ray emitter. An X-ray receiver having a reaction surface, such as a metal mesh comprising a PCO material, may be configured in line with the X-ray emitter. For example, an X-ray receiver, such as a permeable metal mesh coated with PCO material or made from PCO materials, may be configured downstream of the X-ray emitter and receive incident X-rays from the X-ray emitter. An X-ray receiver may extends substantially across the cross-section interior of the conduit, whereby airflow must pass through X-ray receiver as it flows through the conduit. As the air passes through the X-ray receiver, microorganism may be destroyed or oxidized by the X-rays and/or the X-rays incident on the PCO material. Any suitable type of photocatalytic mesh may be used to receive incident X-rays to destroy microorganisms. An X-ray receiver may be configured to produce any suitable pressure drop as the air passes therethrough and may have a frazier value (F) of greater than about 2 F, greater than about 10 F, greater than about 20 F, greater than about 40 F, greater than about 100 F and any range between and including the values provided. A photocatalytic mesh may have an open area of about 30% or more, about 50% or more, about 75% or more, and about 85% or more. An X-ray receiver, such as a photocatalytic mesh may have a mesh size of about 3.175 mm×3.175 mm or more, about 6.35 mm×6.35 mm or more, about 12.7 mm×0.12.7 mm or more, about 25.4 mm×25.4 mm or more, about 50.8 mm×50.8 mm or more, and any range between and including the mesh sizes provided including any combinations of the mesh sized provided such as 3,175 mm×25.4 mm, for example. A photocatalytic mesh may have a mesh strand diameter or cross-flow direction dimension of about 0.254 mm or more, about 1. mm or more, about 2 mm or more, about 3.175 mm, or more, about 6.35 mm or more, and any range between and including the values provided.

An X-ray emitter may be configured upstream of a UV light source, adjacent the UV light source along the length of the conduit, wherein both the UV light source and the X-ray emitter are configured in a common length position along the length of the conduit, or downstream of a UV light source. In an exemplary embodiment, an X-ray emitter is configured upstream of a UV light source and project X-rays down along the length of the conduit, past the UV light source, where the X-rays are incident on an X-ray receiver that is configured downstream of the UV treatment portion.

In this embodiment, the X-rays may be incident on the X-ray receiver and also on the interior walls of the flow conduit along a substantial portion of the length, which may be coated with a PCO material.

An exemplary air treatment system may be configured with a flow deflector feature that is configured to promote air mixing within the conduit and to increase the effectiveness of the disinfecting portion. One or more flow deflectors may be configured along the length of the conduit to promote air mixing as it travels along the length of the conduit. A flow deflector may be a panel that extends along a portion of the length of the conduit or extends circumferentially within the conduit, such as along a portion of the inside surface of the conduit. A flow deflector may be a rib that extend radially out from a center location towards the inside surface of the conduit, or a rib that extends inward from a position more proximal to the inside surface towards a centerline of the conduit. In an exemplary embodiment, a rib extends from the inside surface of the conduit and may be configured as teeth or pleats that increase the surface area of the inside surface of the conduit, thereby increasing disinfecting effectiveness. In another embodiment, a vortex feature is extends in a spiral, or conical shaped spiral to encourage the airflow to spiral around the conduit as it traverses down the length of the conduit. This increase is air resonance time along the inside surface of the conduit may improve disinfecting effectiveness. A vortex feature may be configured around the outside perimeter of a tubular deflector. A tubular deflector may be UV transparent to enable a UV light source within the tubular deflector to pass therethrough.

An exemplary air treatment system may have any suitable size and shape and may be able to treat any suitable flow of air, expressed as cubic feet per minute (CFM) of air, for example. An airflow source, such as a fan, may be configured within the conduit to create an airflow through the conduit. An exemplary air treatment system may be configured to treat air at a velocity through the system of about 200 m/min, or within a range of about 167 m/min to about 228 m/min, or within a range of about 175 m/min to about 220 m/min, or within a range of about 183 m/min to about 213 m/min. The air treatment system may be less effective if the airflow rate or velocity through the system is too high as there may not be enough resonance time for an effective reaction.

An exemplary air treatment system may be configured in any suitable size. In most cases, an air treatment system may be configured to provide about four room air exchanges per hour; or put another way, sized to produce an airflow that is about four times a room's air volume in an hour. In an exemplary embodiment, an air treatment system is configured with an approximately 20 cm (8 in) inlet and is configured to treat approximate 3,680 l/min (130 cfm). In another exemplary embodiment, an air treatment system is configured as a modular system, wherein one or more modules can be removed and replace, or a portion of the module replace and then re-inserted into the air treatment system for airflow at other CFM ratings. For example, a particulate filtration module may be removed and the air filter media replace before re-inserting the module. In another example, the disinfecting portion may comprise a single module compartment wherein UV, TiO2, or soft X-ray modules may be inserted. In this fashion, the most appropriate type of disinfectant component for the application can be inserted into the disinfecting module.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide further understanding of the invention, and are incorporated in and constitute a part of this specification, illustrate embodiments of the invention, and together with the description serve to explain the principles of the invention.

DETAILED DESCRIPTION OF THE ILLUSTRATED EMBODIMENTS

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art, and all such alternate embodiments, combinations, modifications and improvements are within the scope of the present invention.

Figure 1:
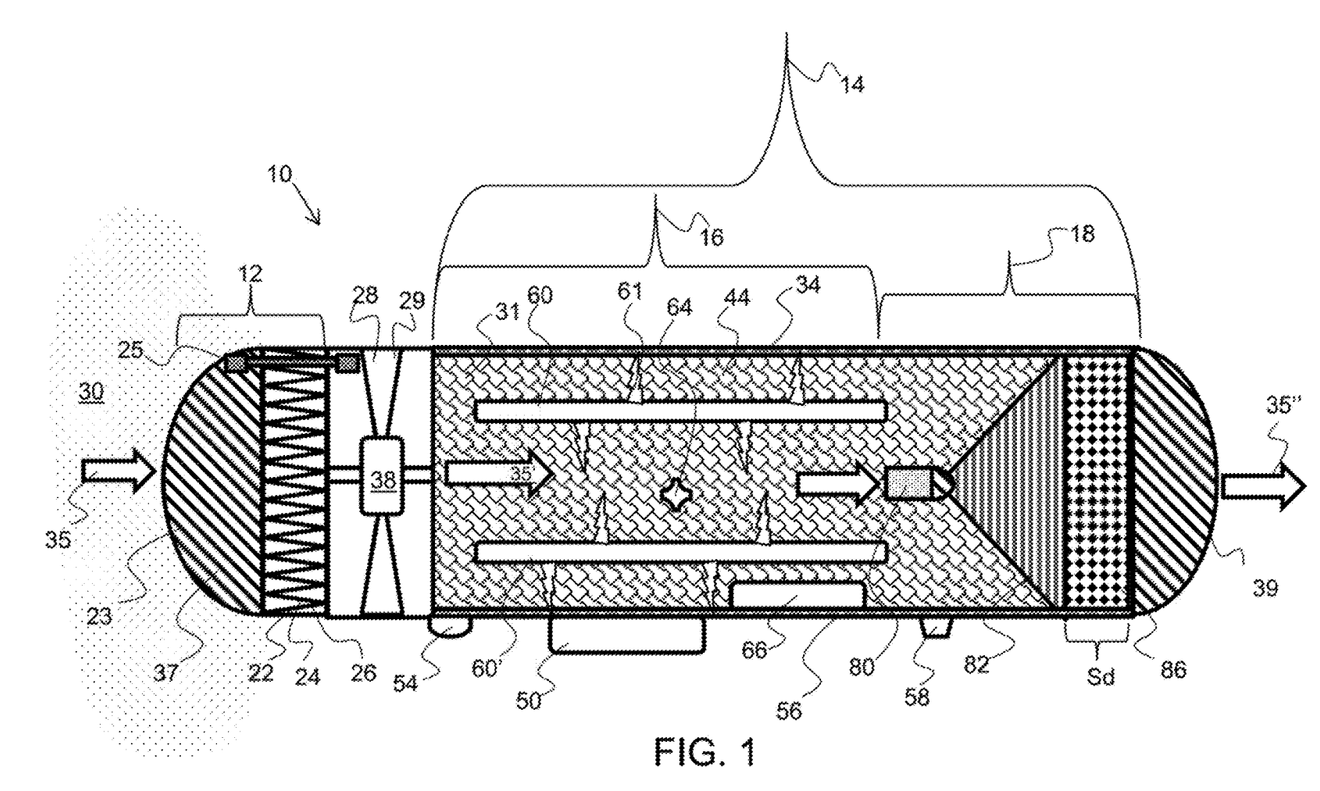
FIG. 1 shows a cross-sectional view of an exemplary air treatment system comprising a particulate filtration portion and a disinfecting portion.

As shown in FIG. 1, an exemplary air treatment system 10 comprises a particulate filtration portion 12 and a disinfecting portion 14. The filtration portion is upstream of the disinfecting portion 14, as indicated by the airflow 35 direction through the air treatment system, indicated by the bold arrow pointing down into the filter portion and the bold arrow pointing out of the disinfecting portion. The filtration portion, and the disinfecting portion are configured within a single and continuous conduit 34. The conduit may be a contiguous conduit made out of a single piece of material and various modules may be incorporated therein. The disinfecting portion 14 comprises a UV treatment portion 16 and an X-ray portion 18. The UV treatment portion comprises a UV light source 60 and a photocatalytic material 44 that is configured along at least a portion of the inside surface 31. The X-ray portion comprises an X-ray emitter configured within the conduit 34 and a photocatalytic mesh 86 configured within the conduit and in line with the projected X-rays from the X-ray emitter.

Figure 2A:
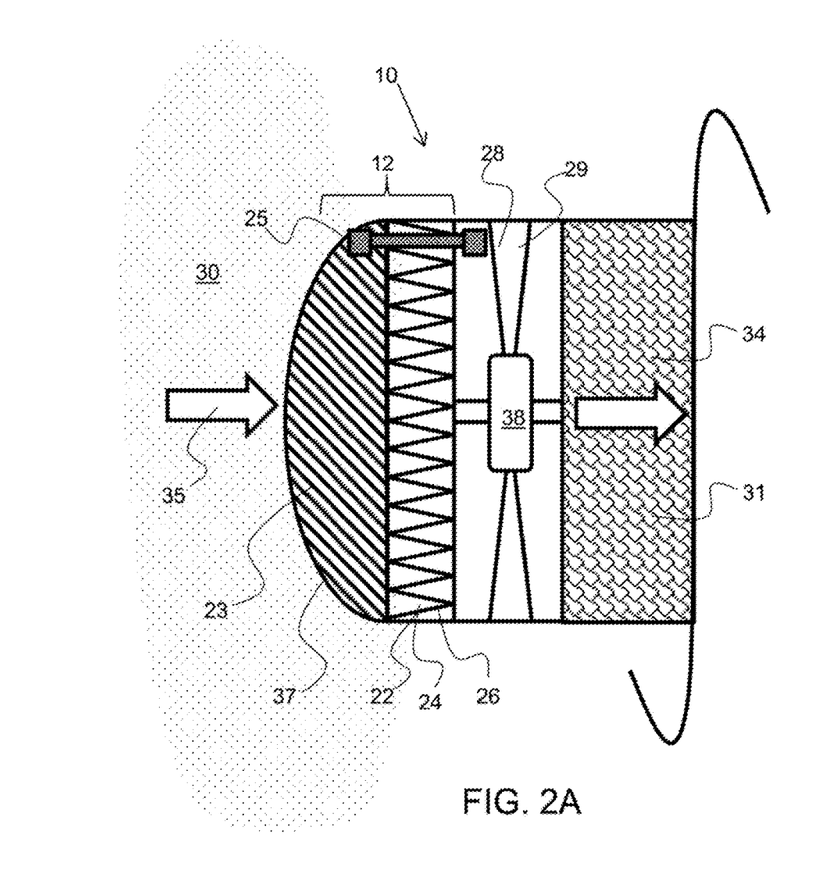
FIG. 2A shows a cross-sectional view an exemplary particulate filtration system.

As shown in FIG. 2A, an exemplary air treatment system 10 comprises a filtration portion 12 having an air filter 20. The air filter, as shown, comprises a filtration media 22 having a plurality of pleats 24. Airflow 35 entering the conduit will pass through the pleats before exiting the particulate filtration portion 12. Pleated filter material increases the area of filtration surface area within an flowthrough area, such as within the conduit. The filtration media may be in the form of a cartridge 26 that would enable quick change out of the media when required. A user may remove the inlet cover 23, which may be a screen to keep large object and particles from entering the system and simply replace the filter cartridge 26. A pressure drop sensor 25, which measures the drop in pressure from the upstream to the downstream side of a filter, may be configured to alert the user when the filter media should be replaced. Generally, the more contamination collected by the filter media, the higher the pressure drop increases.

Figure 2B:
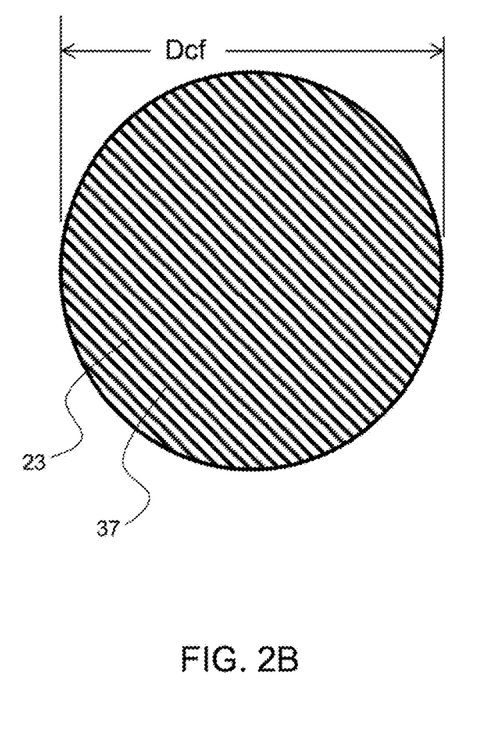
FIG. 2B shows an inlet end view of the exemplary air treatment system shown in FIG. 2A.

FIG. 2B shows the inlet end view of the air treatment system. The conduit is round and has a diameter Dcf. The airflow inlet 37 has an inlet cover 23 configured thereon.

Figure 3A:
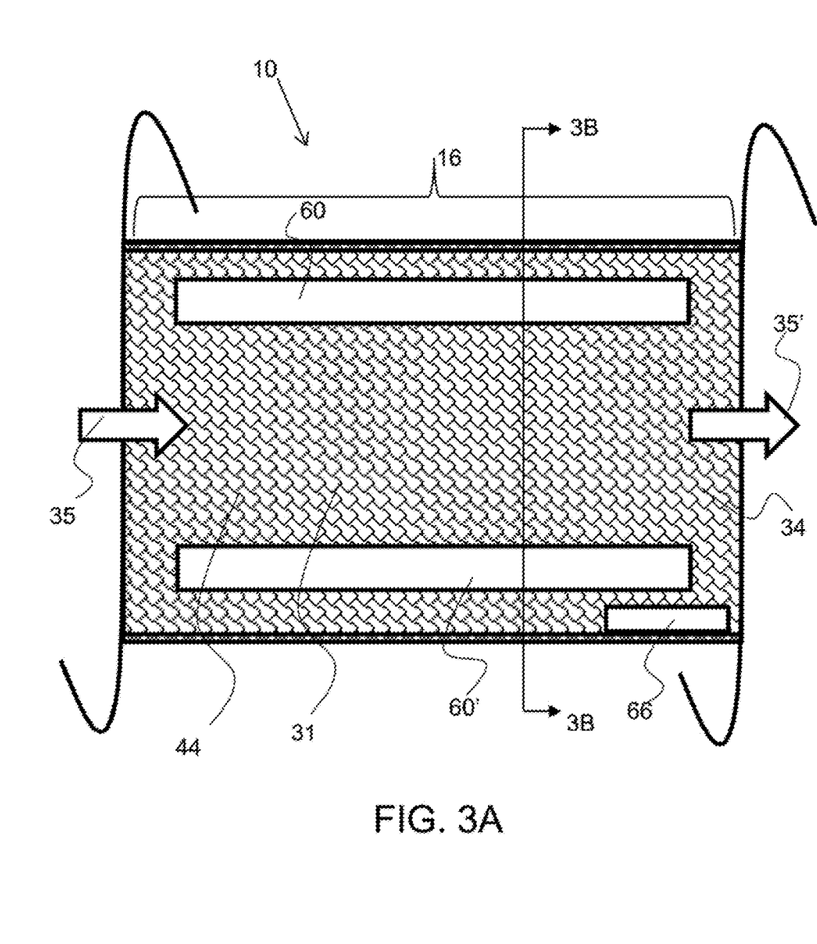
FIG. 3A shows a cross-sectional view of an exemplary UV treatment portion of an exemplary air treatment system having two UV light sources.

As shown in FIG. 3A, an exemplary UV treatment portion 16 comprises a plurality of UV light sources 60, 60' that emit UV light 61 within the conduit 34 and onto the inside surface 31 of the UV treatment portion. The inside surface of the conduit comprises a photocatalyst 44. The photocatalyst reacts with organic materials in the presence of the UV light to destroy bacteria and viruses. The UV ballast is configured within the conduit and powers the UV light sources.

Figure 3B:
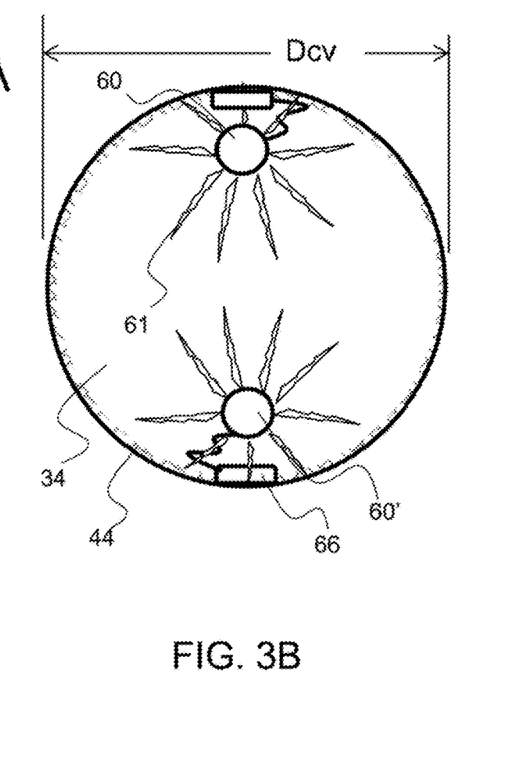
FIG. 3B shows a cross-sectional view along line 3B in FIG. 3A.

As shown in FIG. 3B, two UV light sources 60, 60' are configured within the conduit 34. In this configuration, the two UV light sources are closer to the inside surface 31 of the conduit and therefore the UV light produced may have a higher intensity on a portion of the inside wall than would be provided by a single centrally located UV light source.

Figure 4A:
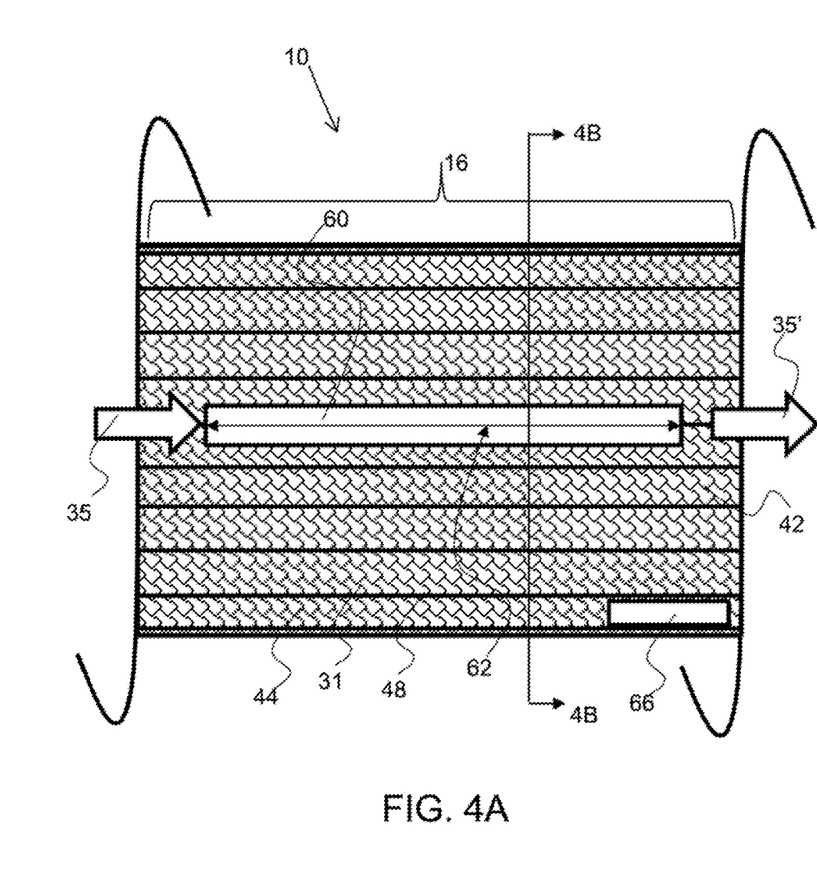
FIG. 4A shows a cross-sectional view of an exemplary UV treatment portion of an exemplary air treatment system having a single centrally located UV light source.
Figure 4B:
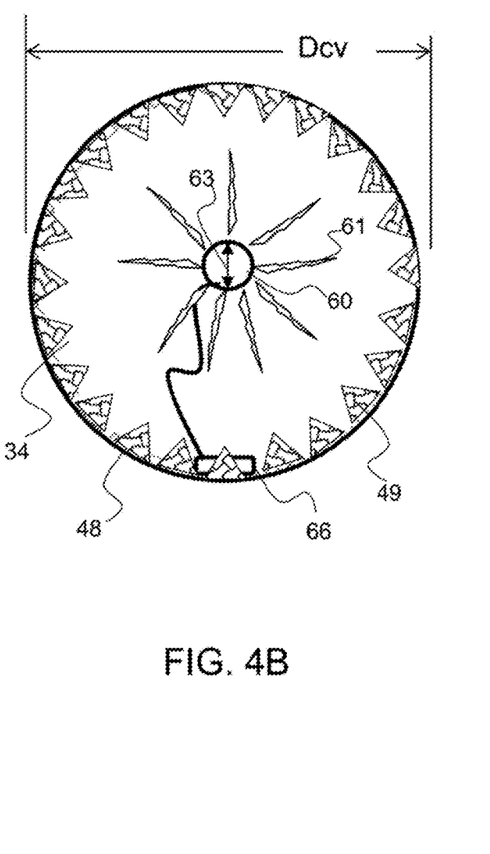
FIG. 4B shows a cross-sectional view along line 4B in FIG. 4A and shows a surface area feature along the inside surface.

As shown in FIGS. 4A and 4B, an exemplary UV treatment portion 16 comprises a surface area feature 48 that increase the effective photocatalytic surface area within the conduit. A plurality of ribs, or raised portions 48 extend up from the inside surface of the conduit and thereby increase the surface area of the photocatalyst. A portion of the inside surface of the conduit may comprise a reflective surface, such as aluminum and may also comprise PCO material. In an exemplary embodiment, a reflective surface is coated or otherwise treated with a PCO material. In another exemplary embodiment, a portion of a reflective surface is coated with PCO material. A pattern of PCO material coating is contemplated to enhance and increase microbial reduction through the air treatment system. For example, on side of a rib, may be coated with PCO material and the other may be a reflective material, thereby producing increased UV light intensity on the opposing PCO coated surface of the rib. The length 62 of the UV light source and the cross-length dimension 63, or diameter in this embodiment, are shown in FIGS. 4A and 4B, respectively. The UV light source is an elongated UV light source as the length is more than three times the cross-length dimension.

Figure 5A:
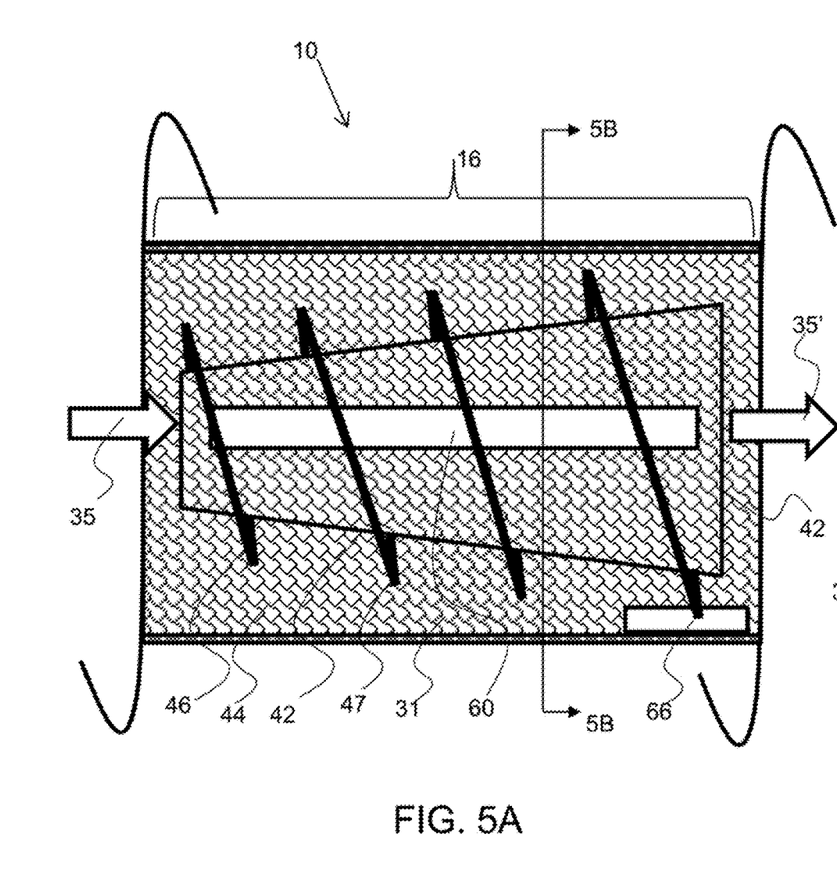
FIG. 5A shows a cross-sectional view of an exemplary UV treatment portion having a flow deflector feature.
Figure 5B:
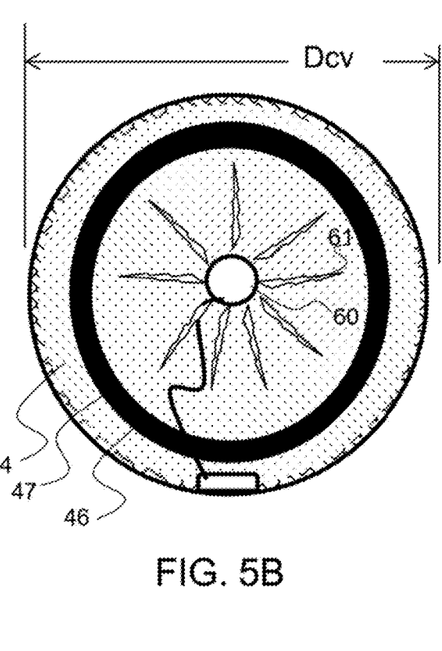
FIG. 5B shows a cross-sectional view along line 58 in FIG. 5A.

As shown in FIGS. 5A and 5B, an exemplary UV treatment portion 16 comprises a flow deflector feature 46 that is configured to increase the amount of air or mixing of air along the inside surface of the conduit. An exemplary flow detector may comprise a fin 45 that directs air to swirl or move in a spiral direction through the conduit. The vortex feature 47 in configured around a tubular deflector 42 and therefore causes a portion of the airflow to swirl or spiral around the tubular deflector and be in close proximity to the inside surface. The tubular deflector shown in conical in shape and may come have a closed end on the upstream side, thereby causing all of the air to spiral or flow around the tubular deflector. In this embodiment, the tubular deflector may be UV light translucent or preferably substantially transparent to enable the UV light to pass therethrough to the inside surface of the conduit. This spiral air flow will increase the amount of air flow along the inside surface and will increase the resonance time of air with the inside surface. Increasing the resonance time of air along the inside surface may increase the effectiveness of microorganisms and/or VOC reduction. A flow detector may comprise a fin that is configured in a spiral configuration as shown. The fins may be any width and may extend substantially to the center of the conduit. The flow deflector may be configured to produce a vortex through the airflow conduit.

Figure 6A:
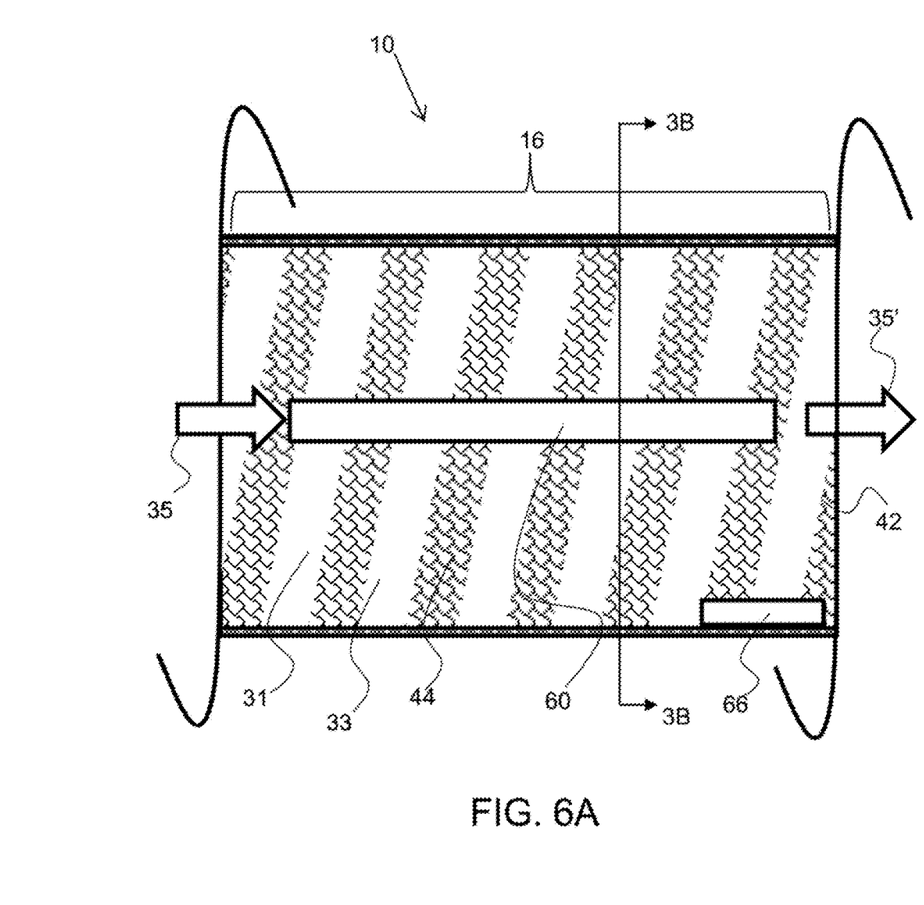
FIG. 6A shows a cross-sectional view of an exemplary UV treatment portion having a reflective fluoropolymer surface.
Figure 6B:
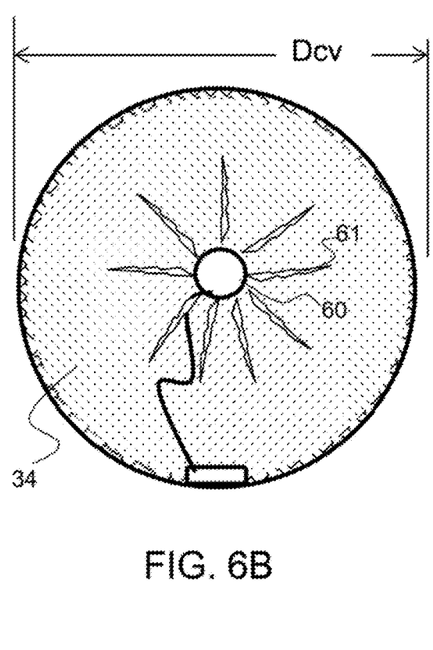
FIG. 6B shows a cross-sectional view along line 6B in FIG. 6A.

As shown in FIGS. 6A and 6B, an exemplary UV treatment portion 16 comprises a reflective surface 34 that is configured over a portion of the inside surface 31. A photocatalyst material 44 is configured over a portion of the inside surface as well. A combination of reflective and PCO surfaces may be configured along the inside surface to enhance reactivity on the PCO material. The reflective and PCO surfaces are configured in alternating bands that spiral down the length of the inside surface of the conduit.

Figure 7A:
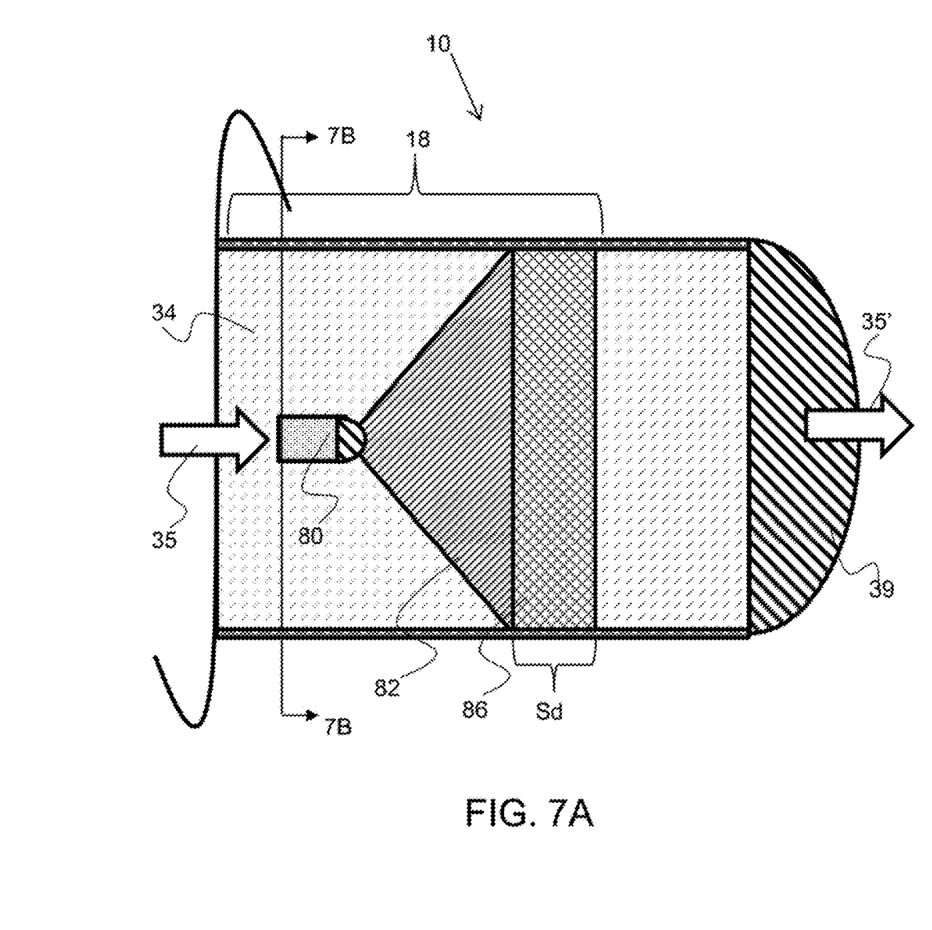
FIG. 7A shows a cross-sectional view of an exemplary X-ray treatment portion.
Figure 7B:
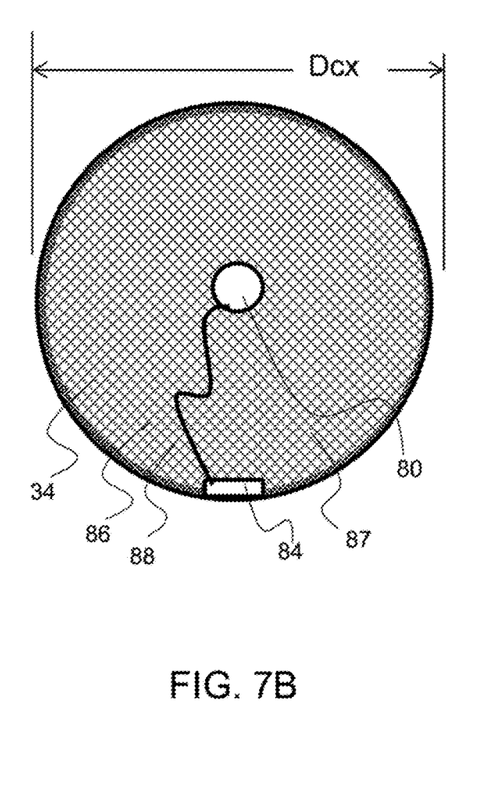
FIG. 7B shows a cross-sectional view along line 7B in FIG. 7A.

As shown in FIGS. 7A and 7B, an exemplary X-ray portion 18 comprises an X-ray emitter 80 that projects X-rays 82 onto a photocatalytic mesh 86. The photocatalytic mesh comprises strands 87 and open areas 88. The photocatalytic mesh comprises a photocatalytic material 44, such as a coating onto a mesh or screen. The photocatalytic mesh is configured within the conduit and airflow 35 passes through the open areas 88 of the mesh. The X-ray emitter is configured within the conduit 34 and projects X-rays 82 in a direction substantially parallel with the airflow direction, or down along the conduit 34.

Figure 9:
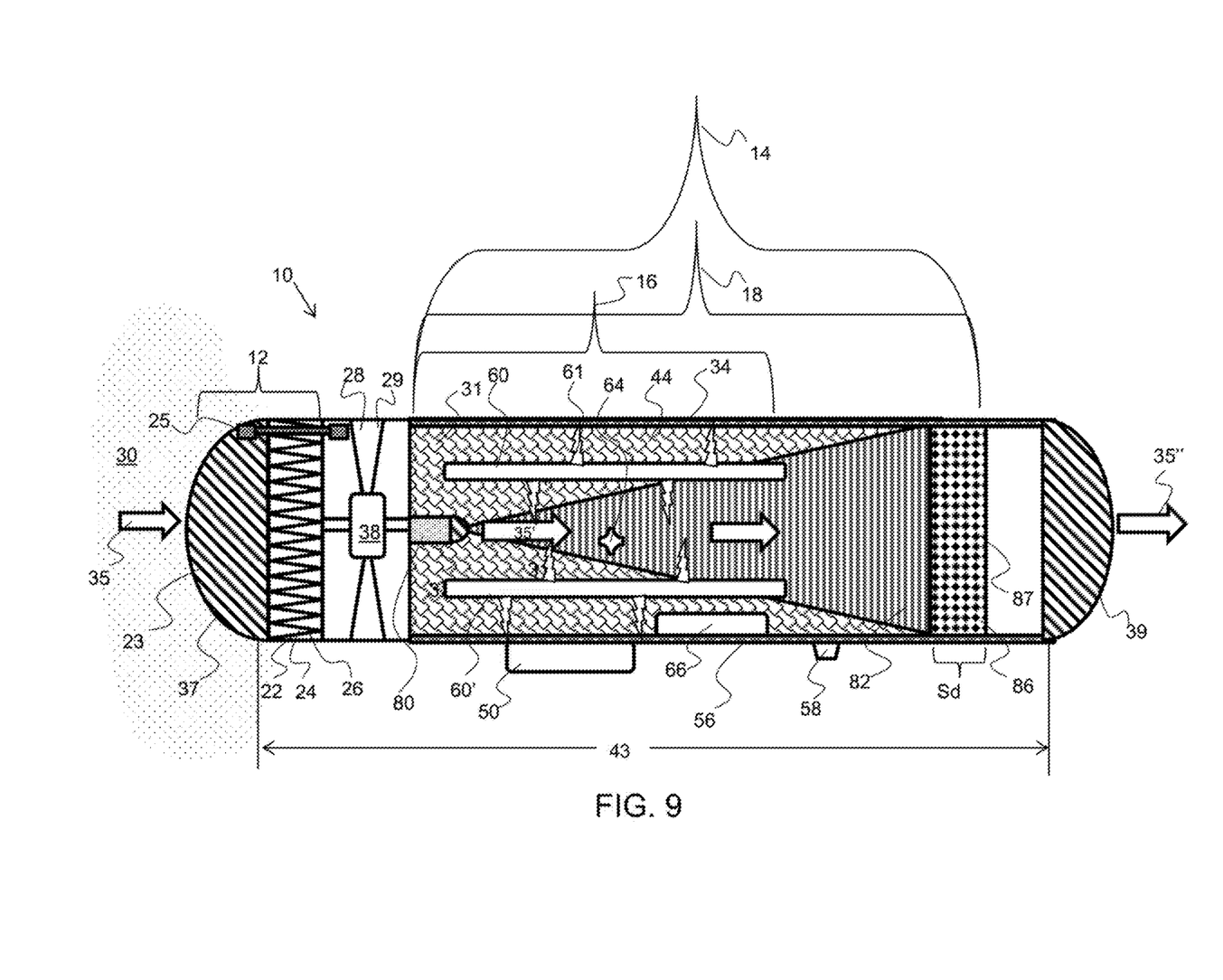
FIG. 9 shows a cross-sectional view of an exemplary air treatment system comprising a particulate filtration portion and a disinfecting portion having an X-ray emitter upstream of a UV light source.

As shown in FIG. 9, an exemplary air treatment system 10 comprises a particulate filtration portion 12 and a disinfecting portion 14. The filtration portion is upstream of the disinfecting portion 14, as indicated by the airflow 35 direction through the air treatment system, indicated by the bold arrows pointing into the filter portion, along the length of the conduit and out of the airflow outlet 39. The filtration portion and the disinfecting portion are configured within a single and continuous conduit 34. The conduit may be a contiguous conduit made out of a single piece of material and various modules may be incorporated therein. The disinfecting portion 14 comprises a UV treatment portion 16 and an X-ray portion 18. The UV treatment portion comprises a UV light source 60 and a photocatalytic material 44 that is configured along at least a portion of the inside surface 31. The X-ray portion comprises an X-ray emitter 80 configured within the conduit 34 and a photocatalytic mesh 86 or X-ray receiver 87 configured within the conduit and in line with the projected X-rays from the X-ray emitter. The X-ray emitter 80 is configured upstream of the UV light source and the X-ray receiver 87 is configured downstream of the UV light source 60. The X-rays 82 are projected substantially along the entire length of the disinfecting portion 14 of the air treatment system 10. The X-rays having a longer resonance time in the conduit compared with the embodiment shown in FIG. 1 may provide more effective disinfecting. The thickness Sd of the X-ray receiver 87 is shown in FIG. 9. The thickness of the X-ray receiver may be provided for effective disinfection of air flowing therethrough. The length 43 of the conduit 34 is shown in FIG. 9. The disinfecting portion 14 is more than 75% of the length of the conduit.

Example 1

Figure 8:
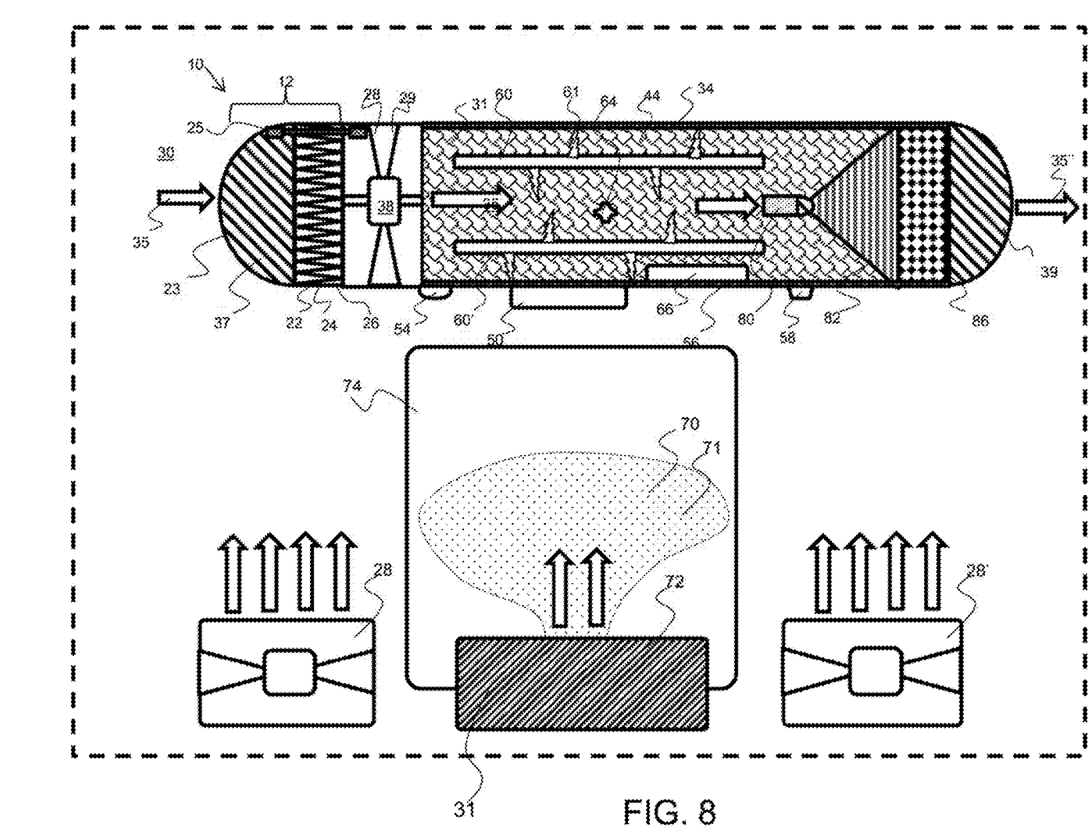
FIG. 8 a diagram of the test apparatus used in Example 1.

A test to measure the effectiveness of an exemplary air treatment system, as described herein was conducted by Antimicrobial Test Laboratories, Round Rock, Tex. An exemplary air treatment system 10 as generally shown in FIG. 8 was tested to determine the quantity of virus destruction versus a control, as described herein. An enclosure 74 that was approximately 4 ft$^3$ was used as an enclosure for the tests. The microorganism, MS2 Bacteriophage 71, ATCC 15597-BI, hereinafter MS2 was used for the study. An aerosol 70 of the MS2 suspension was prepared and homogenized by two circulation fans 28, 28'. MS2 concentrations were measured with and without the air treatment system in operation by the analyzing test suspension samples at the beginning of the test, 20 minutes after the start of the test and 60 minutes after the start of the test. Results showed that the percent reduction in MS2 versus the control was greater than 99% for each of the MS2 collection times when the air treatment system was in operation.

The exemplary air treatment system 10 used in this study comprised a single tubular housing 56 that was approximately 39 in long and 6 in in inner diameter. The air treatment system comprised a particulate filtration portion at the inlet, a UV treatment portion and an X-ray treatment portion. The particulate filtration portion 12 comprised a MERV-8 rated pleated intake filter that was positioned over the airflow inlet 37 of the air treatment system. A 130 CFM output fan 29 was configured within the housing 56 to force air through the conduit 34. The UV treatment portion 16 utilized two a high output UV-C lamps 60, 60' configured within the conduit of the housing. The UV lamps were elongated UV light sources having a length of about 24 inches and a length axis that was substantially aligned with the length axis of the conduit. The two UV lamps were configured on opposing sides of the conduit. The X-ray treatment portion 18 utilized a Moxtek MOX-10 ion cannon X-ray emitter 80, from Moxtek Inc. Orem, Utah. The X-ray emitter was located approximately 7.5 cm (3 in) from four overlapping pieces of galvanized wire mesh 86 having a 2×2 mesh size, 0.464 in opening size, 82% open area, and a 0.04 in diameter wire. The inner diameter of the conduit was lined with a 0.20 in thick silvered aluminum sheet as a reflector. The wire mesh and reflector sheet were covered with PCO material 44, which was applied by mixing $TiO_2$ nanoparticles with spring water to form a paste. The paste was applied with a paper towel, and allowed to dry.

The following procedure was conducted to measure the effectiveness of the air treatment system. A stock suspension of MS2 at a concentration of 2.0×10$^{10}$ PFU/ml was used for the test. A test suspension of MS2 was prepared from the stock suspension by taking an aliquot from the test suspension to achieve a concentration of about 1.0×10$^8$ PFU/ml or more. The microbial concentration of the test suspension was measured prior to initiation of the test, or "time zero", by analysis of test suspension. The test suspension was loaded into a Collison 6-Jet nebulizer and nebulized for 5 minutes before it was aerosolized. The test started at the time the test suspension was aerosolized. Two external fans were configured to homogenize the aerosolized test suspension, inoculum. The time of test was started when the test suspension was aerosolized. A SKC blosampler filled with 20 ml of sterile PBS was used to collect air samples for analysis. The biosampler was exposed to the air for 5 minutes at the beginning of the test, for 5 minutes at the 20 minute period from the start of the test and for 5 minutes at the one hour period from the start of the test. This test was performed with the air treatment system turned one, including the UV treatment portion, X-ray treatment portion and with the air treatment system turned off, for a control. The test was performed with the air treatment system turned off as a control. The air samples from biosampler were incubated to determine microbial concentrations. The reduction in microorganism from the test suspension were calculated. The quantity of microorganisms destroyed by the air treatment system were compared with the control values.

Table 1 provides a summary of the test suspension preparation and use.

TABLE 1

| Test Parameter | MS2 Bacteriophage ATCC 15597-B1 |
| --- | --- |
| Culture Growth Media: | None (Stock Suspension) |
| Culture Growth Time | None |
| Culture Dilution Media | Sterile RP Water |
| Target Inoculum Concentration: | > or = 1.0 × 10$^8$ PFU/ml |
| SKC Biosampler Medium and Volume: | Phosphate Buffered Saline (PBS), 2oml |
| Volume of Inoculum Added to Nebulizer | 10 ml |
| Nebulization Duration | 5 minutes |
| SKC Biosampler Sampling Time | 5 minutes |
| SKC Biosampler Liters (L) Sampled | 62.5 L |
| Enumeration Plating Media: | 50% Tryptic Soy Agar (Supplemented with log phase growth *E. coli* ATCC 155 |
| Enumeration Plate Incubation Time | 18 +/− 6 hours |

Table 2 shows the results of the study. The air treatment system reduced the concentration of microorganisms to 2.24×10$^4$ during the first 5 minute test period, to less than 1.6×10$^1$ PFU/mL at both the 20 minute and at the one hour sample times. These reductions were more than a 99% reduction from the quantity of microorganisms measured for the control, or without the air treatment system being activated.

TABLE 2

| Test Microorganism | Test Group | Prepared Inoculum (CFU/ml) | Sample Time (Post-Nubulization) | Recovery (CFU/m3) | Percent Reduction vs. Respective Control | Log Reduction vs. Respective Control |
|---|---|---|---|---|---|---|
| MS2 Bacteriophage ATCC 15597 | Control (Device | 2.00E+08 | 5 Minutes | 9.68E+05 | N/A | |
| | | | 20 Minutes | 2.31E+05 | | |
| | | | 60 Minutes | 2.60E+04 | | |
| | Treatment (Device | 1.03E+08 | 5 Minutes | 2.24E+0.3 | 99.77% | 2.64 |
| | | | 20 Minutes | <1.6E+01 | 99.99% | 4.16 |
| | | | 60 Minutes | <1.60E+01 | 99.94% | 3.21 |

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they are within the scope of the appended claims and their equivalents.

The invention claimed is:

1. An air treatment system comprising:
a) an airflow conduit comprising:
   i) an inlet;
   ii) an outlet;
   iii) and inside surface;
   iv) a length;
b) a particulate filtration portion comprising:
   i) a particular air filter;
c) a UV treatment portion comprising:
   i) at least one ultraviolet light source configured to emit ultraviolet light onto a portion of the inside surface of the conduit;
   wherein the least one ultraviolet light source is configured within said conduit;
   ii) a photocatalytic surface along at least a portion of the inside surface of the conduit that is exposed to the UV light;
d) an X-ray portion comprising:
   i) a X-ray emitter that emits X-rays down the length of the conduit;
   ii) an air permeable X-ray receiver configured downstream of said X-ray emitter and comprising a photocatalytic material;
wherein the air treatment system is configured to pass an airflow from the inlet to the outlet,
wherein each of said particulate filtration portion, UV treatment portion and X-ray portions are configured in-line with each other and along said conduit; and
wherein the particulate filtration portion is upstream of both the UV treatment portion and the X-ray treatment portion.

2. The air treatment system of claim 1, wherein the least one ultraviolet light source is an elongated UV light source having a length that is at least three times greater than a cross-length dimension.

3. The air treatment system of claim 1, comprising two ultraviolet light sources configured substantially on opposing sides of the conduit.

4. The air treatment system of claim 1, wherein the air treatment system contained in a single housing.

5. The air treatment system of claim 1, further comprising an airflow source configured within said conduit.

6. The air treatment system of claim 1, wherein the photocatalytic surface comprises titanium dioxide.

7. The air treatment system of claim 1, wherein the X-ray emitter is positioned upstream of the at least one UV light source.

8. The air treatment system of claim 7, wherein the X-ray receiver is positioned downstream of the at least one UV light source.

9. The air treatment system of claim 7, wherein the X-ray receiver is positioned upstream of the at least one UV light source.

10. The air treatment system of claim 1, wherein the X-ray emitter is positioned downstream of the at least one UV light source.

11. The air treatment system of claim 1, wherein the X-ray receiver is a metal mesh.

12. The air treatment system of claim 11, wherein the metal mesh has a strand diameter of 0.5 in or less and a percent open area of at least 75%.

13. The air treatment system of claim 1, wherein the X-ray receiver has an air permeability value of at least 10 frazier.

14. The air treatment system of claim 1, wherein the X-ray receiver is configured substantially perpendicular to the length of the conduit and extends substantially across the entire interior conduit;
whereby airflow through the conduit must pass through the X-ray receiver.

15. The air treatment system of claim 1, further comprising an X-ray supply sensor.

16. The air treatment system of claim 1, comprising a surface area feature that increases an inside surface area of the conduit along at least a portion of the length of the airflow conduit.

17. The air treatment system of claim 1, comprising an air deflector future that increase a resonance time of the airflow along the photocatalyst surface.

18. The air treatment system of claim 17, wherein the air deflector feature comprises at least one fin.

19. The air treatment system of claim 1, wherein a portion of the inside surface comprises a reflective material.

20. The air treatment system of claim 1, wherein a controller receives input from a monitoring sensor and wherein said controller activates a status indicator when a threshold value from the monitoring sensor is detected.

21. The air treatment system of claim 20, wherein the monitoring sensor is an ultraviolet light sensor that detects the emitted ultraviolet light from the at least one ultraviolet light source.

22. The air treatment system of claim 1, wherein the conduit is a single continuous conduit.

* * * * *